United States Patent
Kim

(10) Patent No.: US 10,499,881 B2
(45) Date of Patent: Dec. 10, 2019

(54) ULTRASOUND DIAGNOSIS APPARATUS AND METHOD OF DISPLAYING ULTRASOUND IMAGE

(71) Applicant: SAMSUNG MEDISON CO., LTD., Gangwon-do (KR)

(72) Inventor: Han-eol Kim, Gangwon-do (KR)

(73) Assignee: SAMSUNG MEDISON CO., LTD., Hongcheon-gun, Gangwon-do (KR)

( * ) Notice: Subject to any disclaimer, the term of this patent is extended or adjusted under 35 U.S.C. 154(b) by 862 days.

(21) Appl. No.: 14/656,595

(22) Filed: Mar. 12, 2015

(65) Prior Publication Data
US 2015/0257738 A1    Sep. 17, 2015

(30) Foreign Application Priority Data
Mar. 13, 2014    (KR) .......................... 10-2014-0029764

(51) Int. Cl.
*A61B 8/00* (2006.01)
*A61B 8/08* (2006.01)

(52) U.S. Cl.
CPC ............ *A61B 8/468* (2013.01); *A61B 8/0866* (2013.01); *A61B 8/463* (2013.01); *A61B 8/465* (2013.01); *A61B 8/466* (2013.01); *A61B 8/469* (2013.01); *A61B 8/483* (2013.01); *A61B 8/523* (2013.01); *A61B 8/5207* (2013.01); *A61B 8/54* (2013.01)

(58) Field of Classification Search
CPC ............................ A61B 8/0866; A61B 5/4362
See application file for complete search history.

(56) References Cited

U.S. PATENT DOCUMENTS

| | | | |
|---|---|---|---|
| 6,174,285 B1* | 1/2001 | Clark ........................ | A61B 8/14 128/916 |
| 6,306,089 B1* | 10/2001 | Coleman ............. | G01S 7/52023 128/916 |
| 6,983,063 B1 | 1/2006 | Novak et al. | |
| 8,591,420 B2 | 11/2013 | Hamada | |
| 2005/0131293 A1 | 6/2005 | Kato | |

(Continued)

FOREIGN PATENT DOCUMENTS

| | | |
|---|---|---|
| CN | 101534717 A | 9/2009 |
| CN | 101991434 A | 3/2011 |

(Continued)

OTHER PUBLICATIONS

Extended European Search Report issued in corresponding European Patent Application No. 15155239.5, dated Jul. 16, 2015.

(Continued)

*Primary Examiner* — James M Kish
(74) *Attorney, Agent, or Firm* — Morgan, Lewis & Bockius LLP

(57) ABSTRACT

Provided is an ultrasound diagnosis apparatus including: a display unit that displays a first screen including at least one marker; a user interface unit for receiving a selection of a predetermined marker among the at least one marker; and a controller that controls the display unit to display a first screen including a second ultrasound image that represents an object and has a view which is changed according to the predetermined marker. The ultrasound diagnosis apparatus may provide an ultrasound image screen that allows a user to easily and conveniently diagnose an object.

12 Claims, 11 Drawing Sheets

(56) References Cited

U.S. PATENT DOCUMENTS

| | | | |
|---|---|---|---|
| 2009/0076385 A1 | 3/2009 | Jackson et al. | |
| 2009/0153548 A1 | 6/2009 | Rabben et al. | |
| 2010/0030079 A1 | 2/2010 | Hamada | |
| 2011/0046485 A1 | 2/2011 | Nakata | |
| 2011/0255762 A1* | 10/2011 | Deischinger | A61B 8/463 382/131 |
| 2012/0176412 A1 | 7/2012 | Stuebe et al. | |
| 2015/0190112 A1* | 7/2015 | Yeo | A61B 8/0866 600/443 |
| 2015/0272546 A1* | 10/2015 | Cheon | A61B 8/469 600/408 |

FOREIGN PATENT DOCUMENTS

| | | |
|---|---|---|
| JP | 3539323 B2 | 7/2004 |
| JP | 2006-158413 A | 6/2006 |
| WO | 2004/029655 A1 | 4/2004 |

OTHER PUBLICATIONS

Communication pursuant to Article 94(3) EPC issued in corresponding European Patent Application No. 15 155 239.5, dated Sep. 20, 2017.
Office Action issued in Chinese Application No. 201510111664.X dated Jan. 25, 2019, with English translation.

* cited by examiner

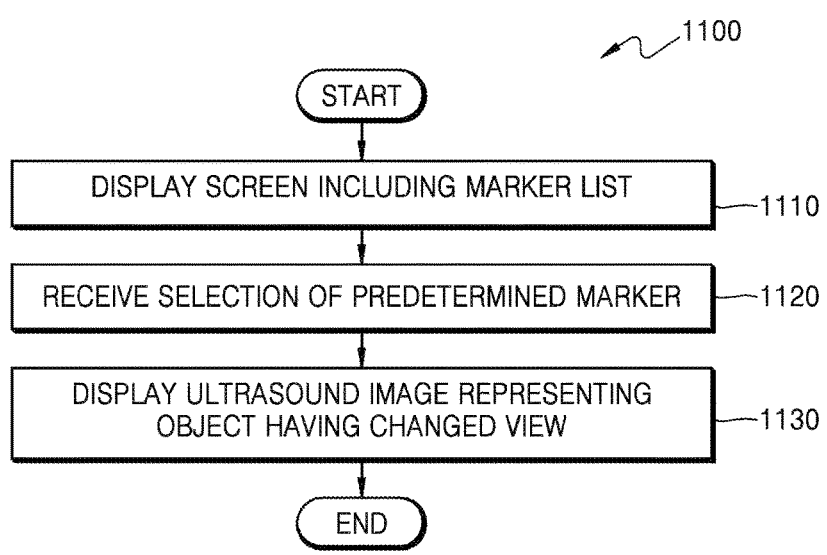

ULTRASOUND DIAGNOSIS APPARATUS AND METHOD OF DISPLAYING ULTRASOUND IMAGE

RELATED APPLICATIONS

This application claims the benefit of Korean Patent Application No. 10-2014-0029764, filed on Mar. 13, 2014, in the Korean Intellectual Property Office, the disclosure of which is incorporated herein in its entirety by reference.

BACKGROUND

1. Field

One or more embodiments of the present invention relate to an ultrasound diagnosis apparatus and a method of displaying an ultrasound image, and more particularly, to an ultrasound diagnosis apparatus and a method of displaying an ultrasound image, which allow a user to easily interpret an ultrasound image.

2. Description of the Related Art

An ultrasound diagnosis device transmits an ultrasound signal generated by a transducer in a probe to an object, receives information about an ultrasound echo signal reflected from the object, and acquires an image of a portion inside the object. In particular, an ultrasound diagnosis device is used for medical purposes such as observation of the internal structure of an object, detection of foreign substances, and measurement of the degree of an injury. An ultrasound diagnosis device has high stability compared to X-ray diagnosis equipment, allows real-time display of an image, and is highly safe due to no exposure to radiation. Therefore, ultrasound diagnosis devices have been widely used together with other types of imaging diagnosis devices.

In general, when a user (e.g., a doctor) interprets an ultrasound image, a marker is set within the ultrasound image for observation of a portion to be examined. Thus, there is a need for an ultrasound diagnosis device and a method of displaying an ultrasound image that allow easy interpretation of an ultrasound image based on a portion indicated by a set marker.

SUMMARY

One or more embodiments include an ultrasound diagnostic apparatus and a method of displaying an ultrasound image that facilitate interpretation of an ultrasound image based on a portion indicated by a marker.

Additional aspects will be set forth in part in the description which follows and, in part, will be apparent from the description, or may be learned by practice of the presented embodiments.

According to one or more embodiments of the present invention, an ultrasound diagnosis apparatus includes: a display unit that displays a first screen including at least one marker; a user interface unit for receiving a selection of a predetermined marker among the at least one marker; and a controller that controls the display unit to display a second screen including a first ultrasound image that represents an object and has a view which is changed according to the predetermined marker.

The controller may change the view of the object based on position information of the predetermined marker and information about a viewpoint corresponding to the predetermined marker.

The apparatus may further include a memory for storing the position information of the predetermined marker and the information about the viewpoint corresponding to the predetermined marker.

The first screen may include a second ultrasound image representing an object and a marker list comprises the at least one marker.

The marker list may include the at least one marker indicating a predetermined point of the object or at least one marker representing a display view of the object.

When the object is a fetus, the marker list may include at least one marker representing a display view of the object for measuring biometrics.

When the object is a fetus, the marker list may also include at least one marker representing a display view of the object for diagnosing whether the fetus is normally growing.

The user interface unit may receive a selection of at least one marker from a user in order to generate the marker list.

The controller may extract at least one marker representing a display view for diagnosing the object or measuring a part of the object.

The marker list may include at least one of the at least one extracted marker and at least one marker selected by the user.

The controller may assign the at least one marker to a group based on a distance between markers and generate the marker list including a sub-marker list containing the at least one marker assigned to the group.

The controller may assign the at least one marker to a group according to each part of the object and generate the marker list including a sub-marker list containing the at least one marker assigned to the group.

The user interface unit may output an edit menu for generating an ultrasound moving image based on at least one ultrasound image corresponding to the at least one marker included in the marker list.

The controller may control the apparatus so that the ultrasound moving image generated based on the at least one ultrasound image corresponding to the at least one marker selected through the edit menu is played back.

In order to play back the ultrasound moving image, the user interface unit may receive at least one of a playback duration of an ultrasound image corresponding to a selected marker, information about image effects applied to the ultrasound image, and audio information related to the ultrasound image.

The controller may control playback of the ultrasound moving image based on the playback duration, the information about image effects, and the audio information.

Each item of the marker list may comprises at least one of information about a part of the object corresponding to a marker, information about a display view of the object corresponding to the marker, information about measurable biometrics corresponding to the marker, and the second ultrasound image.

According to one or more embodiments of the present invention, a method of displaying an ultrasound image includes: displaying a first screen including at least one marker; receiving a selection of a predetermined marker among the at least one marker; and displaying a second screen including a first ultrasound image that represents an object and has a view which is changed according to the predetermined marker.

The method may further include changing the view of the object based on position information of the predetermined marker and information about a viewpoint corresponding to the predetermined marker.

The ultrasound diagnosis apparatus and the method of displaying an ultrasound image according to the embodiments of the present invention may provide an ultrasound image screen that allows a user to easily and conveniently diagnose an object.

In detail, the ultrasound diagnosis apparatus and the method of displaying an ultrasound image facilitate convenient diagnosis of a portion of an object in which a position where a marker is set is located at a center.

BRIEF DESCRIPTION OF THE DRAWINGS

These and/or other aspects will become apparent and more readily appreciated from the following description of the embodiments, taken in conjunction with the accompanying drawings in which:

FIG. 11 is a flowchart of a method of displaying an ultrasound image according to an exemplary embodiment of the present invention.

DETAILED DESCRIPTION

Figure 1:
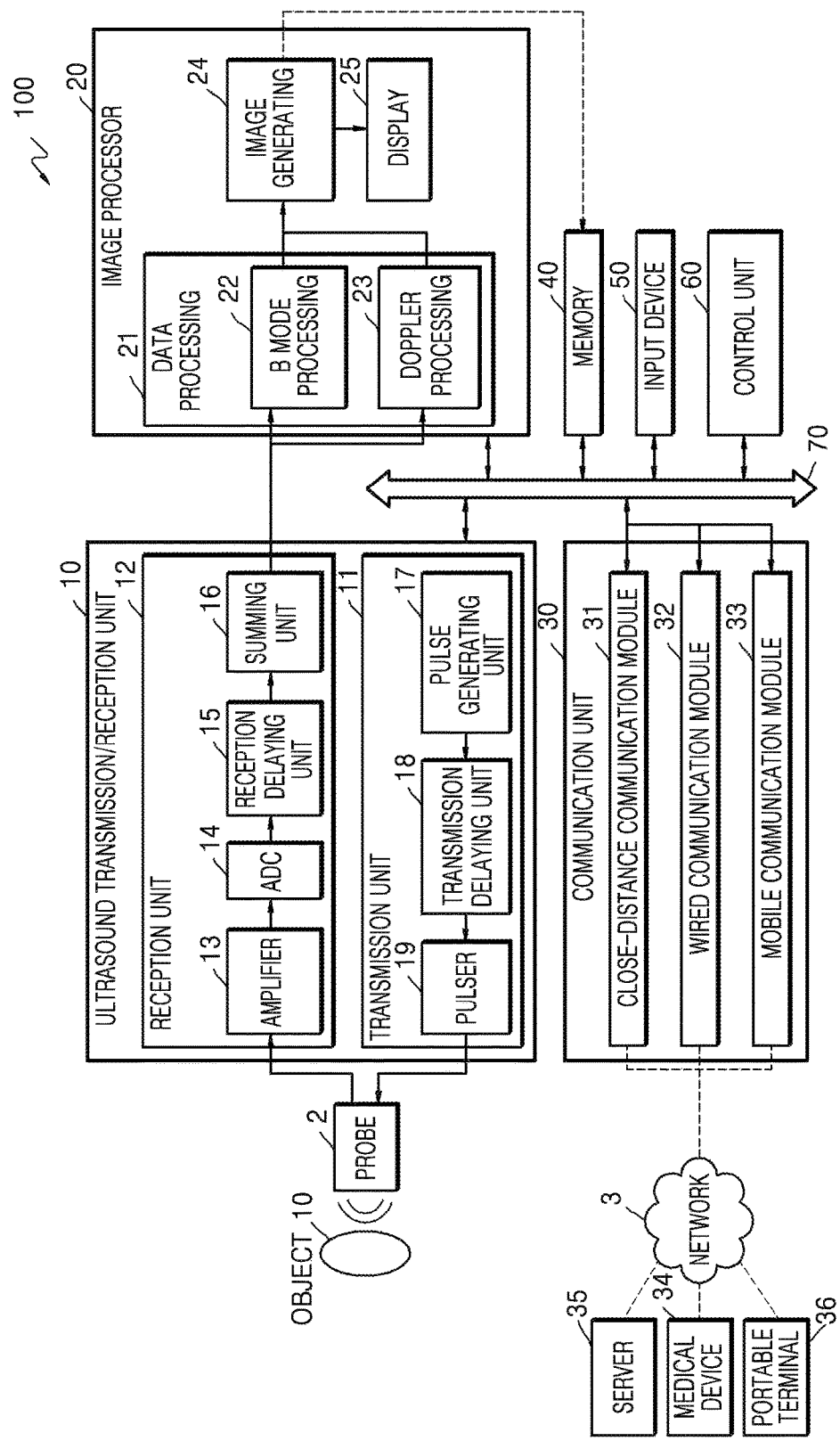
FIG. 1 illustrates an overall configuration of an ultrasound diagnosis device used in embodiments of the present invention.

Exemplary embodiments of the present invention will now be described more fully hereinafter with reference to the accompanying drawings so that they may be easily implemented by one of ordinary skill in the art. However, the present embodiments may have different forms and should not be construed as being limited to the descriptions set forth herein. In addition, parts not related to the present invention are omitted to clarify the description of exemplary embodiments of the present invention. In the accompanying drawings, like reference numerals refer to like elements throughout.

Throughout the specification, it will be understood that when an element is referred to as being "connected" or "coupled" to another element, it can be directly connected to or electrically coupled to the other element with one or more intervening elements interposed therebetween. Throughout the specification, it will also be understood that when a part "includes" or "comprises" an element, unless there is a particular description contrary thereto, the part can further include other elements, not excluding the other elements. In addition, terms such as " . . . unit", " . . . module", or the like refer to units that perform at least one function or operation, and the units may be implemented as hardware or software or as a combination of hardware and software. As used herein, the term "and/or" includes any and all combinations of one or more of the associated listed items. Expressions such as "at least one of," when preceding a list of elements, modify the entire list of elements and do not modify the individual elements of the list.

Throughout the specification, an "ultrasonic image" refers to an image of an object obtained using an ultrasonic wave. Furthermore, in the present specification, an "object" may include a person or an animal, or a part of a person or an animal. For example, the object may include organs such as the liver, the heart, the womb, the brain, a breast, and the abdomen, or a blood vessel. Furthermore, the "object" may include a phantom. A phantom is a material having a volume that approximately equal to the density and effective atomic number of a living organism.

Furthermore, in the present specification, a "user" refers to a medical professional, such as a doctor, a nurse, a medical laboratory technologist, and a medical imaging expert, and a technician who repairs a medical apparatus, but the user is not limited thereto.

The embodiments of the present invention will now be described in detail with reference to the accompanying drawings.

FIG. 1 illustrates an overall configuration of an ultrasound diagnosis device 100 used in embodiments of the present invention.

Referring to FIG. 1, the ultrasound diagnosis device 100 includes a probe 2, an ultrasound transmission/reception unit 10, an image processor 20, a communication unit 30, a memory 40, an input device 50, and a controller 60, and the components may be connected to one another via buses 70.

The ultrasound diagnosis device 100 may be embodied not only as a cart type device but also as a portable device. Examples of portable ultrasound diagnosis apparatuses may include a Picture Archiving and Communications System (PACS) viewer, a smartphone, a laptop computer, a personal digital assistant (PDA), and a tablet PC. However, the present invention is not limited thereto.

The probe 2 transmits ultrasound signals to an object 1, based on a driving signal applied by the ultrasound transmission/reception unit 10, and receives echo signals reflected from the object 1. The probe 2 includes a plurality of transducers that oscillate based on electric signals transmitted thereto and generate acoustic energy, that is, ultrasound waves. Furthermore, the probe 2 may be connected to a main body of the ultrasound diagnosis device 100 by wires or wirelessly. According to embodiments of the present invention, the ultrasound diagnosis device 100 may include a plurality of probes 2.

A transmission unit 11 supplies a driving signal to the probe 2 and includes a pulse generator 17, a transmission delaying unit 18, and a pulser 19. The pulse generator 17 generates pulses for forming transmission ultrasound waves based on a predetermined pulse repetition frequency (PRF), and the transmission delaying unit 18 applies a delay time to the pulses in order to determine transmission directionality of the pulses. Pulses, to which a delay time is applied, correspond to a plurality of piezoelectric vibrators included in the probe 2, respectively. The pulser 19 applies a driving signal (or a driving pulse) to the probe 2 at a timing corresponding to each pulse to which a delay time is applied.

A reception unit 12 generates ultrasound data by processing echo signals received from the probe 2. The reception unit 12 may include an amplifier 13, an analog-to-digital converter (ADC) 14, a reception delaying unit 15, and a summing unit 16. The amplifier 13 amplifies echo signals in each channel, and the ADC 14 performs analog-to-digital conversion on the amplified echo signals. The reception delaying unit 15 applies delay times for determining reception directionality to the echo signals subjected to the analog-to-digital conversion, and the summing unit 16 generates ultrasound data by summing the echo signals processed by the reception delaying unit 15. According to embodiments of the present invention, the reception unit 12 may not include the amplifier 13. In other words, if the sensitivity of the probe 2 or the capability of the ADC 14 to process bits is enhanced, the amplifier 13 may be omitted.

The image processor 20 generates an ultrasound image by scan-converting ultrasound data generated by the ultrasound transmission/reception unit 10 and displays the ultrasound image. In addition, an ultrasound image may include not only a gray-scale ultrasound image obtained by scanning an object in an amplitude (A) mode, a brightness (B) mode, and a motion (M) mode, but also a Doppler image representing a moving object by using the Doppler effect. The Doppler image may include a blood flow Doppler image (also called a color Doppler image) showing a flow of blood, a tissue Doppler image showing movement of tissue, and a spectral Doppler image showing the speed at which an object moves as a waveform.

A B mode processor 22 extracts B mode components from ultrasound data and processes the B mode components. An image generator 24 may generate an ultrasound image in which signal intensities are represented as brightness based on the extracted B mode components.

Similarly, a Doppler processor 23 may extract Doppler components from ultrasound data, and the image generator 24 may generate a Doppler image indicating movement of an object as colors or waveforms based on the extracted Doppler components.

The image generator 24 according to an embodiment of the present invention may generate a three-dimensional (3D) ultrasound image via volume-rendering of volume data and an elasticity image which shows the degree of deformation of the object 1 due to pressure. Furthermore, the image generator 24 may display additional information in an ultrasound image by using text and graphics. In addition, the generated ultrasound image may be stored in the memory 40.

A display unit 25 displays and outputs the generated ultrasound image. The display unit 25 may display and output not only an ultrasound image, but also various information processed by the ultrasound diagnosis device 100, on a screen via a graphical user interface (GUI). In addition, the ultrasound diagnosis device 100 may include two or more display units 25 according to embodiments of the present invention.

The communication unit 30 is connected to a network 3 by wires or wirelessly and communicates with an external device or server. The communication unit 30 may exchange data with a hospital server or another medical device in a hospital that is connected via a Picture Archiving and Communications System (PACS). Furthermore, the communication unit 30 may perform data communication according to the Digital Imaging and Communications in Medicine (DICOM) standard.

The communication unit 30 may transmit or receive data related to diagnosis of the object 1, e. g., an ultrasound image, ultrasound data, and Doppler data of the object 1, via the network 3. The communication unit 30 may also transmit or receive medical images obtained by other medical devices, such as a CT image, an MR image, and an X-ray image. Furthermore, the communication unit 30 may receive information related to a diagnosis history or a treatment schedule of a patient from a server and utilize the information to diagnose the patient, i.e., the object 1. Furthermore, the communication unit 30 may perform data communication with a server or a medical device in a hospital as well as a portable terminal of a doctor or a patient.

The communication unit 30 is connected to the network 3 in a wired or wireless manner and may exchange data with a server 35, a medical device 34, or a portable terminal 36. The communication unit 30 may include at least one component that enables communication with an external device, e.g., a local area communication module 31, a wired communication module 32, and a mobile communication module 33.

The local area communication module 31 is a module for performing local area communication with a device that is within a predetermined distance. Examples of local area communication technology include a wireless Local Area Network (LAN), Wi-Fi, Bluetooth, ZigBee, Wi-Fi Direct (WFD), Ultra Wideband (UWB), Infrared Data Association (IrDA), Bluetooth Low Energy (BLE), and Near Field Communication (NFC), but are not limited thereto.

The wired communication module 32 is a module for performing communication by using an electric signal or an optical signal. Examples of wired communication technology include wired communication technologies using a pair cable, a coaxial cable, an optical fiber cable, and an Ethernet cable.

The mobile communication module 33 transmits or receives wireless signals to or from at least one of a base station, an external terminal, and a server on a mobile communication network. Here, the wireless signals may include voice call signals, video call signals, or various types of data for transmission and reception of text/multimedia messages.

The memory 40 stores various data processed by the ultrasound diagnosis device 100. For example, the memory 40 may store not only medical data related to the diagnosis of the object 1, such as ultrasound data and ultrasound images that are input or output, but also algorithms or programs that are executed in the ultrasound diagnosis device 100.

The memory 40 may be embodied as any of various storage media such as a flash memory, a hard disk drive, and Electrically Erasable Programmable Read-Only Memory (EEPROM). Furthermore, the ultrasound diagnosis device 100 may utilize a web storage or a cloud server that functions as the memory 40 online.

The input device 50 is a means via which a user inputs data for controlling the ultrasound diagnosis device 100. The input device 50 may include hardware components, such as a keypad, a mouse, a touch panel, a touch screen, a trackball, and a jog switch. However, the present invention is not limited thereto, and the input device 50 may further include various other input elements such as an electrocardiogram measuring module, a respiration measuring module, a voice recognition sensor, a gesture recognition sensor, a fingerprint recognition sensor, an iris recognition sensor, a depth sensor, a distance sensor, etc.

The controller 60 may control overall operations of the ultrasound diagnosis device 100. In other words, the controller 60 may control operations among the probe 2, the ultrasound transmission/reception unit 10, the image processor 20, the communication unit 30, the memory 40, and the input device 50.

All or some of the probe 2, the ultrasound transmission/reception unit 10, the image processor 20, the communication unit 30, the memory 40, the input device 50, and the controller 60 may be implemented as software modules. However, the present invention is not limited thereto, and some of the above components may be implemented as hardware modules. Furthermore, at least one of the ultrasound transmission/reception unit 10, the image processor 20, and the communication unit 30 may be included in the controller 60, but the present invention is not limited thereto.

In order to diagnose disease by using an ultrasound image including an object, a marker may be set in the ultrasound image for determining a portion of the object to be examined or indicating a predetermined position of the object.

In detail, the marker may be set in a portion of the object that needs to be carefully observed for a user to diagnose a patient's disease or identify the presence of an abnormality in the patient. In order to more accurately diagnose a portion of an object in which the above-described marker is set, an ultrasound diagnosis apparatus configured to output a modified ultrasound image and a method of displaying an ultrasound image are provided.

Figure 2:
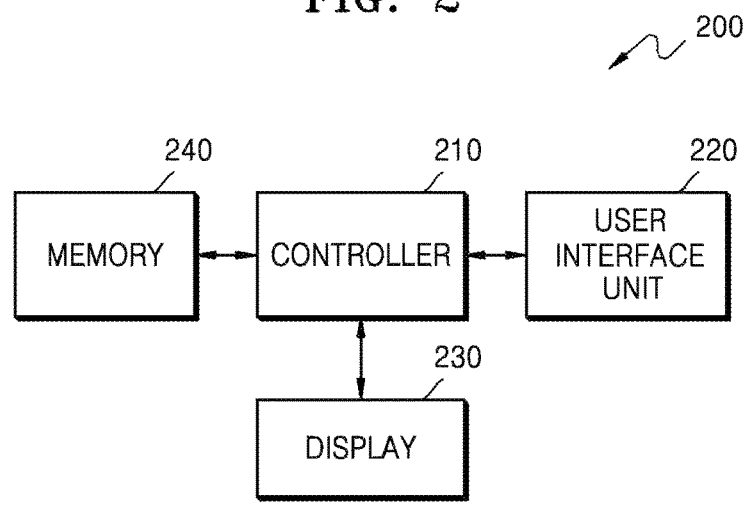
FIG. 2 illustrates an ultrasound diagnosis apparatus according to an exemplary embodiment of the present invention.

FIG. 2 illustrates an ultrasound diagnosis apparatus 200 according to an exemplary embodiment of the present invention.

Referring to FIG. 2, the ultrasound diagnosis apparatus 200 according to the present embodiment includes a controller 210, a display unit 230, and a user interface unit 220. The ultrasound diagnosis apparatus 200 may further include a memory 240.

Furthermore, the ultrasound diagnosis apparatus 200 may be incorporated into the ultrasound diagnosis device 100 shown in FIG. 1. In detail, the controller 210, the display unit 230, the user interface unit 220, and the memory 240 correspond to the image generator 24, the display unit 25, the input device 50, and the memory 40, respectively.

Furthermore, the ultrasound diagnosis apparatus 200 may correspond to the medical device 34 or the portable terminal 36, respectively, and receive ultrasound data acquired by the ultrasound diagnosis device 100 via the network 3 for use.

The display unit 230 displays a first screen including at least one marker. In detail, the display unit 230 may display a first screen that includes a marker list containing the at least one marker. Herein, the marker list may include the at least one marker indicating a predetermined point of the object or at least one marker representing a display view of the object. Furthermore, the first screen may further include a first ultrasound image representing an object. Here, the first ultrasound image is generated using ultrasound data acquired by scanning the object via a probe, and may include at least one of a two-dimensional (2D) ultrasound image and a 3D ultrasound image. Furthermore, a marker may be set at a predetermined point of an object or in a predetermined portion or region of the object. For example, the marker may be set at a diagnostically meaningful point in an object, or in a predetermined organ corresponding to a portion of the object to be examined. For example, if the object is a fetus, a marker may be set at a point on the back of the fetus's neck in order to measure a Nuchal Translucency (NT) thickness. As another example, a marker may be set in a fetus's head in order to measure sizes of the fetal head and cerebral ventricles within the fetal brain.

The user interface unit 220 receives selection of a predetermined marker among the at least one marker. In detail, the user interface unit 220 may receive selection of a predetermined marker in a marker list included in the screen displayed on the display unit 230. The user interface unit 220 may also generate a user interface screen via which a predetermined input may be received from a user. The user interface screen may also be generated by the controller 210. The display unit 230 may then display the user interface screen generated by the user interface unit 220 or the controller 210. For example, the first screen may be a user interface screen including a marker list for receiving selection of a predetermined marker from the user, and may be generated by the user interface unit 220 or the controller 210.

The controller 210 controls the display unit 230 to display a second screen including a second ultrasound image corresponding to a predetermined marker selected via the user interface unit 220. Here, the second ultrasound image represents an object and has a view which is changed according to the predetermined marker.

In detail, the controller 210 may generate an ultrasound image by scan-converting ultrasound data acquired by scanning an object. For example, a 2D ultrasound image generated by the controller 210 may include not only a gray-scale ultrasound image obtained by scanning an object in an A mode, a B mode, and a M mode, but also a Doppler image representing a moving object by using a Doppler effect.

The controller 210 may extract B mode components from ultrasound data and generate a B mode ultrasound image in which signal intensities are represented as brightness based on the extracted B mode components. Furthermore, the controller 210 may extract Doppler components from ultrasound data and generate a Doppler image indicating movement of an object as colors or waveforms based on the extracted Doppler components.

Furthermore, the controller 210 may generate volume data by using ultrasound data and produce a 3D ultrasound image by performing volume-rendering on the volume data.

In addition, the controller 210 may not generate an ultrasound image therein but receive an ultrasound image corresponding to an object from the outside. For example, the ultrasound diagnosis apparatus 200 may receive an ultrasound image from another ultrasound diagnosis apparatus (not shown).

The display unit 230 may display a first screen including a marker list and a first ultrasound image received or generated by the controller 210.

In detail, the user interface unit 220 may generate and output a user interface screen for receiving a predetermined command or data via a user input. The user interface unit 220 may receive the predetermined command or data from the user via the user interface screen. The user may recognize predetermined information when viewing the user interface screen displayed through the display unit 230, and input a predetermined command or data via the user interface unit 220.

For example, the user interface unit 220 may include a mouse, a keyboard, or another input device including hard keys for receiving a predetermined command or data via a user input. For example, the user may enter predetermined data or command by manipulating at least one of the mouse, the keyboard, and the other input device in the user interface unit 220.

In another example, the user interface unit 220 may be formed as a touch pad. In detail, the user interface unit 220 may include a touch pad (not shown) combined with a display panel (not shown) in the display unit 230. In this case, the user interface screen may be output to the display panel. Then, when a predetermined command is input via the user interface screen, the touch pad detects information corresponding to the predetermined command and transmits the detected information to the controller 210. Then, the controller 210 interprets the detected information and recognizes and executes the predetermined command input by the user.

In detail, if the user interface unit 220 is formed as a touch pad, when the user touches a predetermined point on the user interface screen, the user interface unit 220 detects a position of the touched point and transmits the detected position to the controller 210. The controller 210 may then recognize a user request or command corresponding to a menu displayed at the detected position and execute the recognized user request or command.

An example where the controller 210 generates a user interface screen and outputs the user interface screen to the display unit 230, and the user interface unit 220 receives predetermined data or command from a user and transmits the predetermined data and command to the controller 210 will now be described in detail.

In detail, the controller 210 generates a marker list and then a first screen including the marker list and outputs the first screen. Then, the display unit 230 displays the first screen. If the user interface unit 220 is formed as the above-described touch pad, the user selects a predetermined marker by touching a point which is on the displayed first screen and indicated by the predetermined marker in the marker list. Then, the controller 210 may recognize the selection of the predetermined marker and control the display unit 230 to display a second screen that includes an ultrasound image that represents an object and has a view that is changed according to the predetermined marker. A screen displayed on the display unit 230 will now be described in more detail with reference to FIG. 3.

Figure 3:
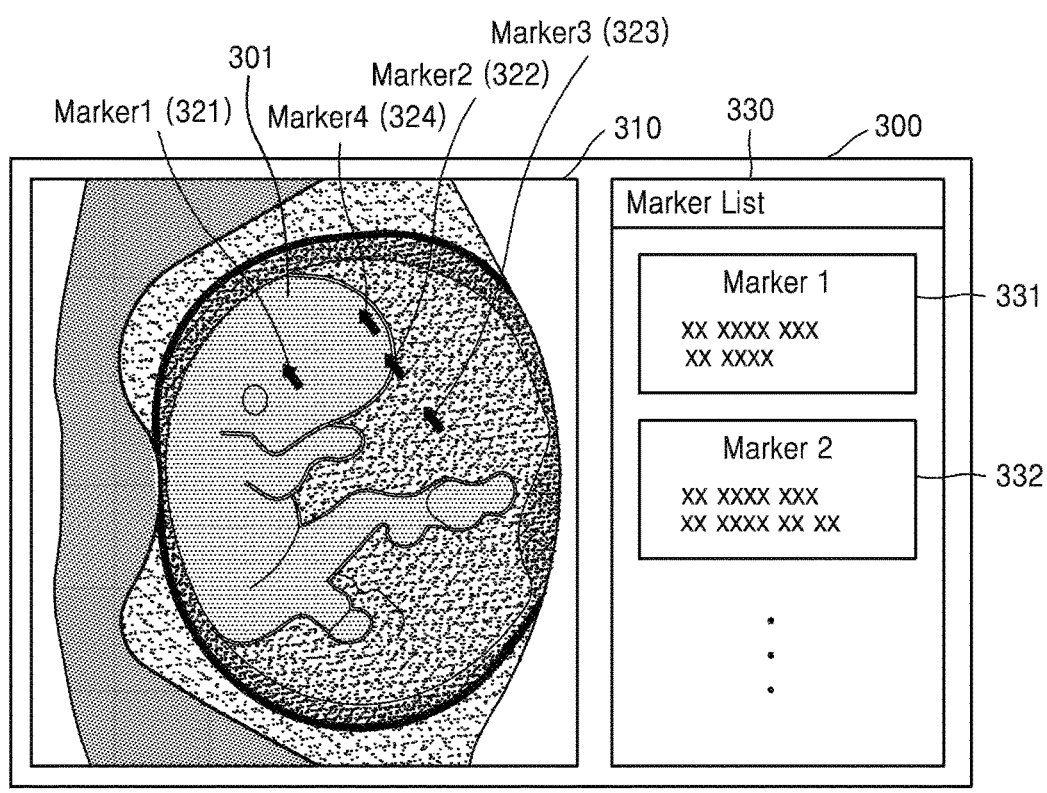
FIG. 3 illustrates a screen generated in an ultrasound diagnosis apparatus according to an exemplary embodiment of the present invention.

FIG. 3 illustrates a screen generated in an ultrasound diagnosis apparatus according to an exemplary embodiment of the present invention, and more particularly, a first screen 300 displayed on the display unit 230 according to control of the controller 210.

Referring to FIG. 3, the first screen 300 includes a first ultrasound image 310 and a marker list 330. The first screen 300 is an ultrasound image acquired by performing an ultrasound scan on an object 301. In FIG. 3, the object 301 is a fetus, and the first ultrasound image 310 is a 3D ultrasound image.

The marker list 330 includes at least one marker item.

For example, if a marker indicates a predetermined portion or region in an ultrasound image or object 301, as shown in FIG. 3, the marker may not be displayed as a marker (e.g., a first marker 321) indicating a predetermined point within the first ultrasound image 310. In this case, the marker may not be displayed in the first ultrasound image 310. Instead, an image (not shown) showing the predetermined portion or region may be included in each marker item of the marker list 330 so that the user visually recognizes the marker indicating the predetermined portion or region.

Furthermore, if a marker is set at a predetermined point within an ultrasound image or object, the marker (e.g., the first marker 321) may be displayed so as to indicate the predetermined point in the first ultrasound image 310, as shown in FIG. 3.

The first marker 321 may have an arrow shape as shown in FIG. 3 or other various shapes such as a circular shape, a polygonal shape, a hand shape, a cross shape, etc. The first marker 321 may also have various colors that can be represented by using 24-bit Red, Green, Blue (RGB) values.

In detail, the marker list 330 may include at least one marker item corresponding to a marker representing a display view of the object 301. For example, each marker item included in the marker list 330 may include an ultrasound image having a display view corresponding to a marker set at a predetermined point within the first ultrasound image 310 or the object 301.

At least one of first through fourth markers 321 through 324 may also be displayed on the object 301 in the first ultrasound image 310. Alternatively, each of the first through fourth markers 321 through 324 may be displayed at a predetermined point in the first ultrasound image 310 and not on the object 301. The marker list 330 is a list of the at least one of the first through fourth markers 321 through 324 located on the first ultrasound image 310, and a marker item of the market list 330 may include information about each of the first through fourth markers 321 through 324. For example, first and second marker items 331 and 332 may include information about the first marker 321 and about the second marker 322, respectively.

Each marker item (e.g., first marker item 331) of the marker list 330 may include at least one of information about a point or part of the object 301 corresponding to a marker, information about a display view of the object 301 corresponding to the marker, information about measurable biometrics corresponding to the marker, and a second ultrasound image having the marker at the center thereof.

Here, the information about a point or part of the object 301 refers to information about a body point or a body part of the object 301 where a marker is located and may include a name of the body point or body part such as the head, face, torso, arms, legs, the abdomen, or chest, or a name of an organ in which the marker is located, such as the cerebellum, cerebrum, heart, or stomach. In detail, if the object 301 is a fetus, the information about a point or part of the object 301 may include names of body parts such as the head, face, eyes, lips, spine, gastrointestinal (GI) tract, adrenal gland, kidney, bladder, external genitalia, anus, umbilical cord insertion, arms, hands, legs, feet, diaphragm, lungs, heart, etc.

The information about a display view refers to information about a frontal view of the object 301 where a marker is located and may include information about displayed planes of the object 301 such as a sagittal plane, a coronal plane, a horizontal or axial plane, a mid-sagittal plane, etc. In detail, a 'display view' refers to a frontal view of the object appearing on a screen and in which a marker is positioned at the center thereof.

The information about measurable biometrics refers to information about biometrics that can be accurately measured from a view representing a front part of an object with a marker at the center thereof. Biometrics refers to biological information of physical characteristics or traits of a human and includes all values used to determine normality in a human body. For example, fetal biometrics may include Gestational Sac (GS), Crown Rump Length (CRL), Biparietal Diameter (BPD), Head Circumference (HC), Abdominal Circumference (AC), Femur Length (FL), Anterior Posterior Thoracic Diameter (APTD), Thorax Transverse Diameter (TTD), Occipital Frontal Diameter (OFD), Outer Ocular Distance (OOD), Humerus (HUM), NT, and Nasal Bone.

The second ultrasound image contained in each marker item (e. g., first marker item 331) of the marker list 330 means an ultrasound image representing an object of which a view is changed to correspond to a marker. The second ultrasound image may be an ultrasound image representing the front of the object 301 where the marker is located.

The second ultrasound image may be included in each marker item of the marker list 330 as a thumbnail image.

The user may request display of a second ultrasound image by selecting a predetermined marker item (e. g, the first marker item 331). Alternatively, the user may request display of the second ultrasound image by selecting a predetermined marker (e.g., the first marker 321) displayed on the first ultrasound image 310. According to the above user selection, the controller 210 may control the display unit 230 to display the second ultrasound image.

Figure 4:
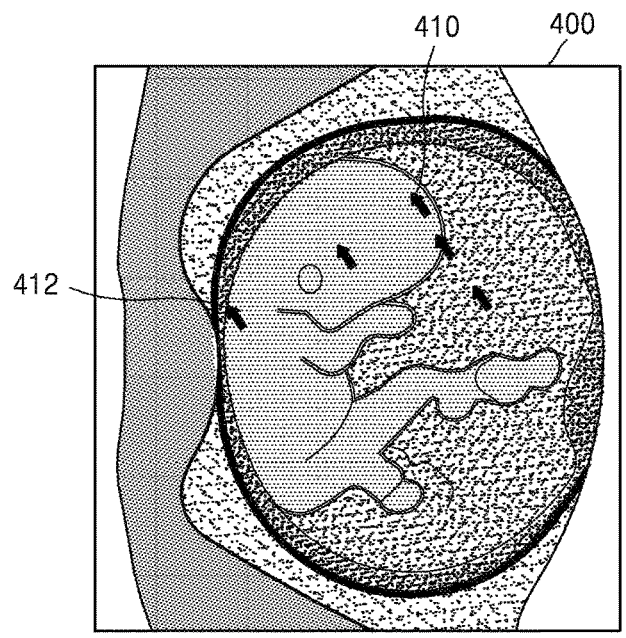
FIG. 4 is a diagram for explaining an operation of an ultrasound diagnosis apparatus according to an exemplary embodiment of the present invention.

FIG. 4 is a diagram for explaining an operation of an ultrasound diagnosis apparatus 200 according to an exemplary embodiment of the present invention.

As described above, a marker may be automatically set by the controller 210 or input directly by a user.

In detail, the controller 210 may automatically set at least one marker representing a display view for diagnosing an object or measuring a portion of the object. For example, in order to diagnose whether the object has a disease or abnormality, the controller 210 may automatically extract a portion of the object having a risk of a disease or disorder and automatically set a marker in the portion of the object. For example, if the result of analysis of an ultrasound image shows that a tumor is present in the object, a marker may be set at a central portion of the tumor so that the details of the tumor are displayed.

Furthermore, the controller 210 may automatically set at least one marker representing a display view for measuring a portion of the object and biometrics.

Referring to FIG. 4, when an object 401 is a fetus, the controller 210 may set as a marker 410 a central point of a front of a head that is a portion of the object 401 necessary to determine whether a brain of the object 401 is growing at a normal rate.

Furthermore, if the marker 410 is extracted and included in a marker list, when a user selects the marker 410 from the marker list, a second screen including a second ultrasound image may be displayed. In this case, the second ultrasound image includes the front of the head in which the marker 410 is located at a center of the second screen. Furthermore, the controller 210 may set a point for measuring an NT as a marker 412. If the marker 412 is set and included in a marker list, when a user selects the marker 412 from the marker list, a second screen including a second ultrasound image may be displayed. In this case, the second ultrasound image shows a cross-section of the fetal NT with the marker 412 located at a center of the second screen.

Furthermore, the user interface unit 220 may receive at least one marker from the user. Referring to FIG. 4, the user may set markers 410 and 412 at predetermined points in a displayed first ultrasound image 400.

Figure 5:
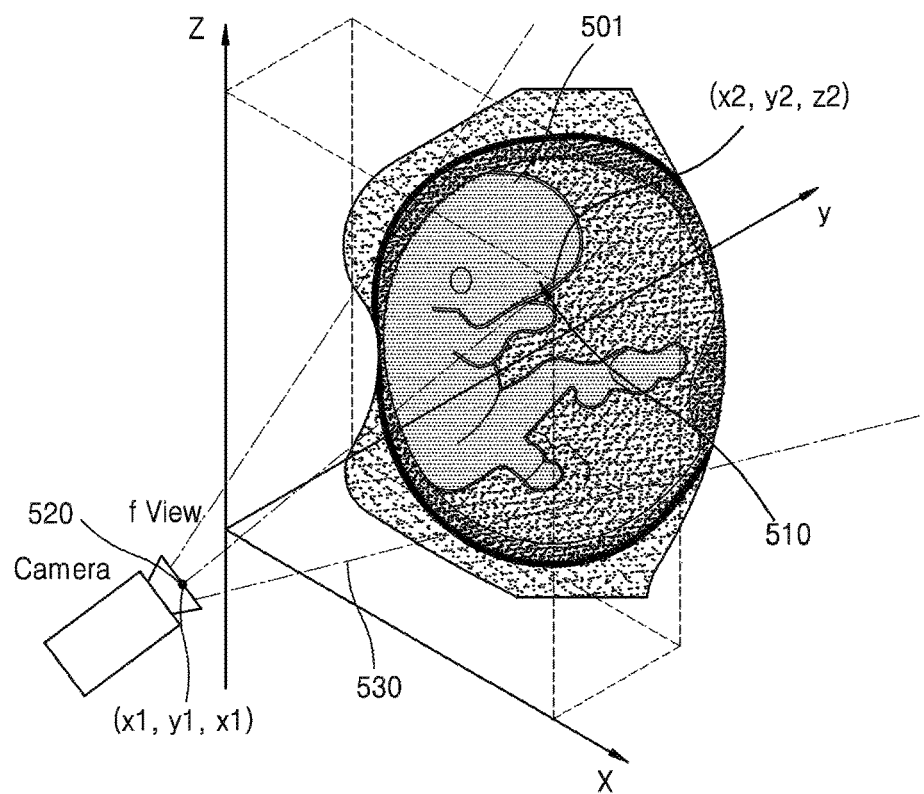
FIG. 5 is a diagram for explaining an operation of an ultrasound diagnosis apparatus according to another exemplary embodiment of the present invention.

FIG. 5 is a diagram for explaining an operation of an ultrasound diagnosis apparatus 200 according to another exemplary embodiment of the present invention.

The controller 210 may change a view of an object based on position information of a marker and information about a viewpoint corresponding to the marker. The position information and the information about the viewpoint may be stored together when the marker is set. It is hereinafter assumed that an ultrasound image on which the marker is set is a 3D ultrasound image.

In detail, the memory 240 may store position information of a marker and information about a viewpoint corresponding to the marker. If there are a plurality of markers, the memory 240 may store identification (ID) information that is used to distinguish each of the plurality of markers as well as the position information of the marker and the information about the viewpoint that are mapped to the ID information. The ID information of the marker may be created as a combination of letters and numbers. Furthermore, the ID information may be designated for each marker by a user. For example, if an ID number is used as ID information of a marker, the memory 240 may assign 'marker1' as an ID number of the first marker, map position information of the first marker and information about the viewpoint to the ID number marker1, and store the ID number 'marker 1' and the position information of the first marker and the information about the viewpoint. Position information of a marker and information about a viewpoint corresponding to the marker will now be described in more detail with reference to FIG. 5.

Referring to FIG. 5, a marker 510 may be set on an object 501 in a 3D ultrasound image 500. Position information of the marker 510 may be coordinate information of the marker 510 in a 3D coordinate system with a predetermined reference point (0,0,0) as an origin. The position information of the marker 510 may include at least one of Cartesian coordinates and Euler coordinates.

'Information about a viewpoint corresponding to a marker' may mean position information of a viewpoint 520 corresponding to a display view 530 with a marker 510 located at a center thereof. More specifically, it is assumed that an image having the display view 530 with the marker 510 at the center thereof is captured by using a virtual camera. In this case, the display view 530 with the marker 510 at the center thereof may be a view captured by a camera having the viewpoint 520. Here, the marker 510 may be located at the center of the display view 530, and a viewpoint corresponding to the marker 510 may mean the viewpoint 520 of the display view 530 having the marker 510 at the center thereof.

The information about the viewpoint 520 corresponding to the marker 510 may include at least one of Cartesian coordinates and Euler coordinates.

Figure 6:
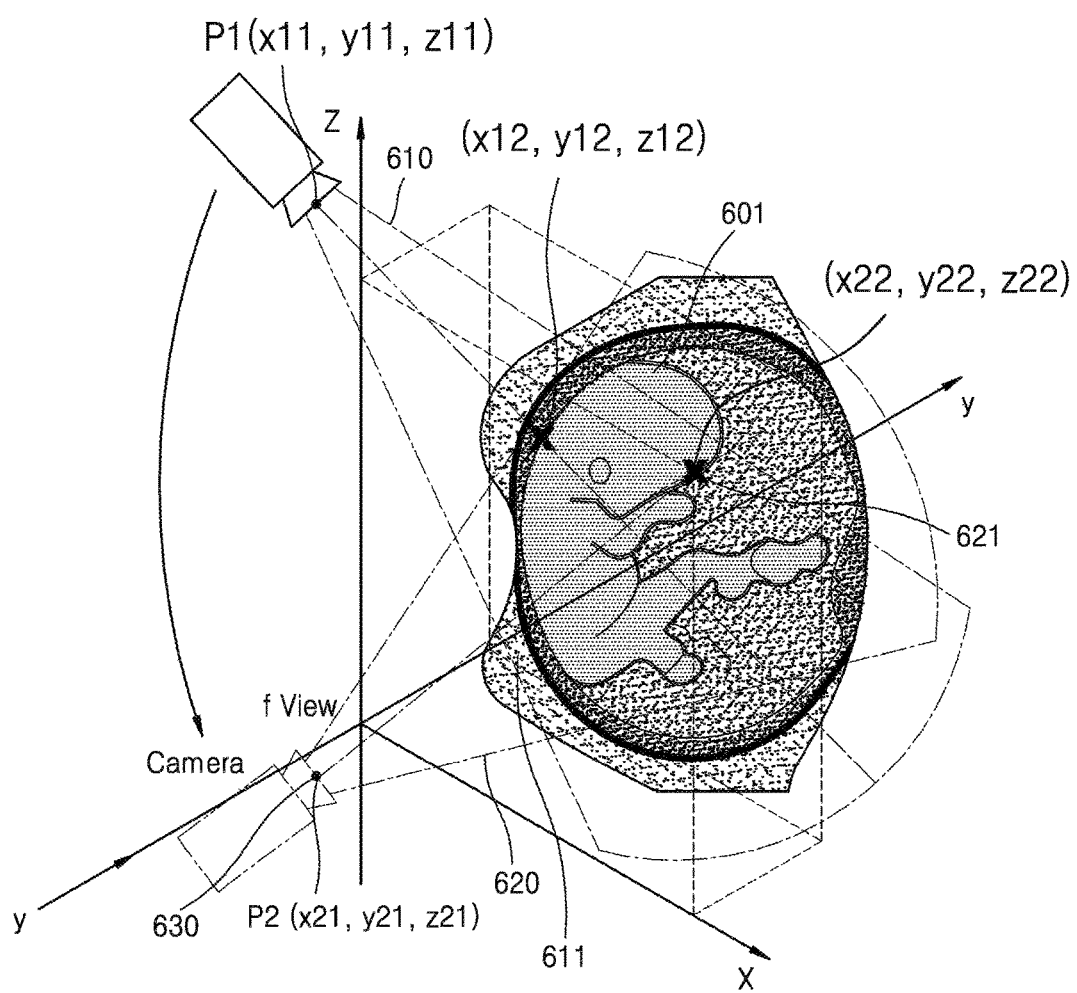
FIG. 6 is a diagram for explaining an operation of an ultrasound diagnosis apparatus according to another exemplary embodiment of the present invention.

FIG. 6 is a diagram for explaining an operation of the ultrasound diagnosis apparatus 200 according to another exemplary embodiment of the present invention.

Referring to FIG. 6, a first ultrasound image representing a display view 610 having a viewpoint P1 (x11, y11, z11) may be included in and displayed on a first screen. In this case, since the viewpoint P1 (x11, y11, z11) corresponds to a viewpoint of a virtual camera when an object, i.e., a fetus 601, is captured from a rear side of the fetus 601, the first ultrasound image may be an ultrasound image showing the back of the fetus 601. For example, the first ultrasound image may have the display view 610 with a marker 611 set at point (x12, y12, z12) on the back of the fetus 601 and located at a center thereof.

When a user selects a marker 621 set at a predetermined point (x22, y22, z22) on the right side of a head of the fetus 601 from a menu marker list, the controller 210 may control the display unit 230 to display a second ultrasound image that represents the fetus 601 and has a view which is changed to correspond to the marker 621. In other words, when the marker 621 is selected, the controller 210 may control the display unit 230 to display a second ultrasound image having a display view 620 corresponding to the marker 621.

As described above, the controller 210 may change a view of the object based on position information of the selected marker 621 and information about a viewpoint corresponding to the selected marker 621. In detail, the memory 240 stores position coordinates (x12, y12, z11) of the marker that are mapped to the marker and position coordinates (x11, y11, z11) of the viewpoint P1 corresponding to the marker. The memory 240 may also store position coordinates (x22, y22, z22) of the marker 621 mapped to the marker 621 and position coordinates (x21, y21, z21) of the viewpoint P2 corresponding to the marker 621. When the marker 621 is selected, the controller 210 calculates a variation between a position of the viewpoint P1 of the first ultrasound image currently being displayed and a changed position of the viewpoint P2 of the first ultrasound image by using the position coordinates (x11, y11, z11) and (x21, y21, z21) of the viewpoints P1 and P2. The controller 210 then moves a view representing the fetus 601 according to the calculated variation. The controller 210 may also perform rendering on ultrasound data obtained by scanning the fetus 601 and generate a 3D ultrasound image. Alternatively, other various image processing techniques may be used to change a view according to a change in a viewpoint.

Figure 7A:
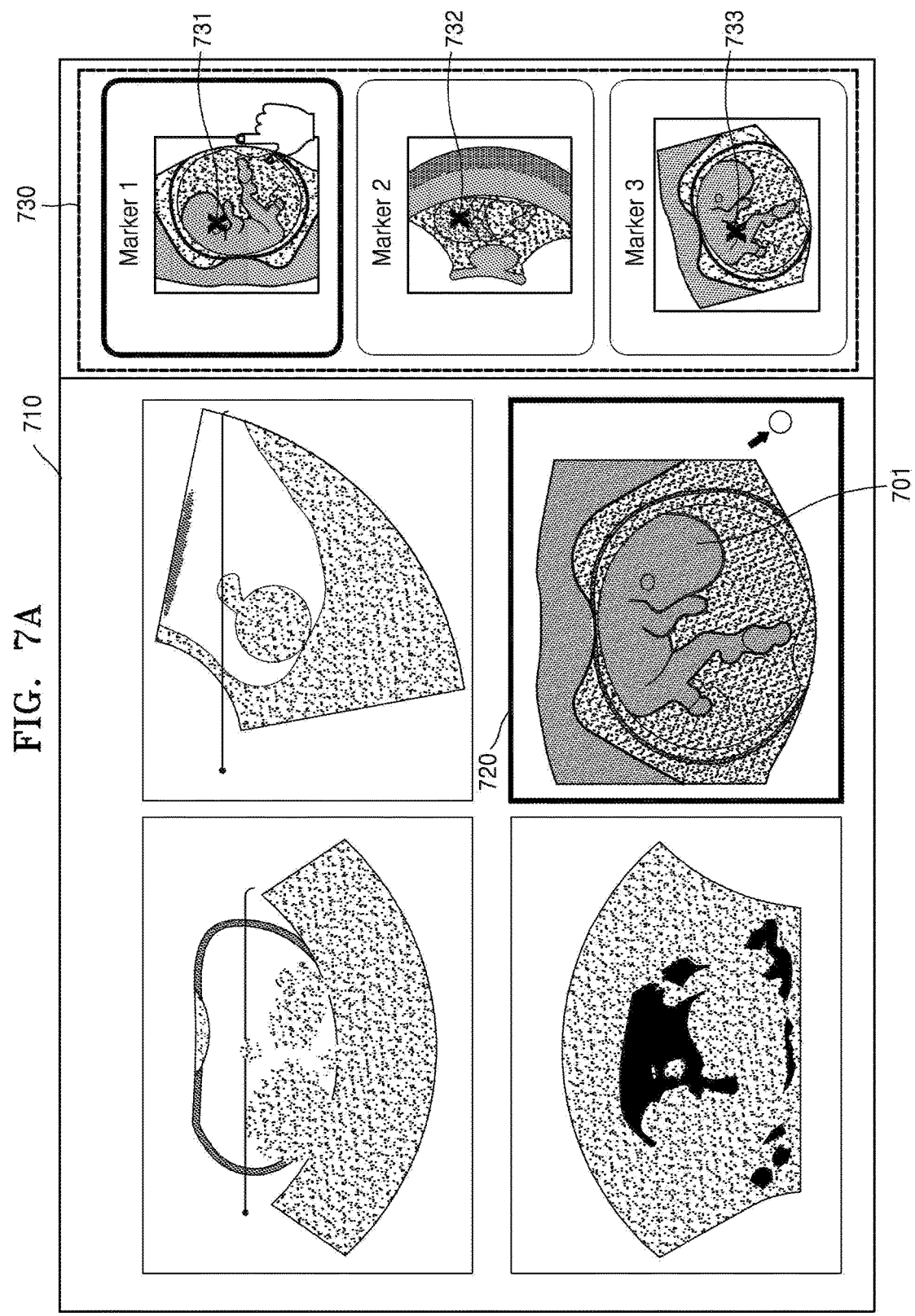
FIG. 7A is a diagram for explaining an operation of an ultrasound diagnosis apparatus according to another exemplary embodiment of the present invention.
Figure 7B:
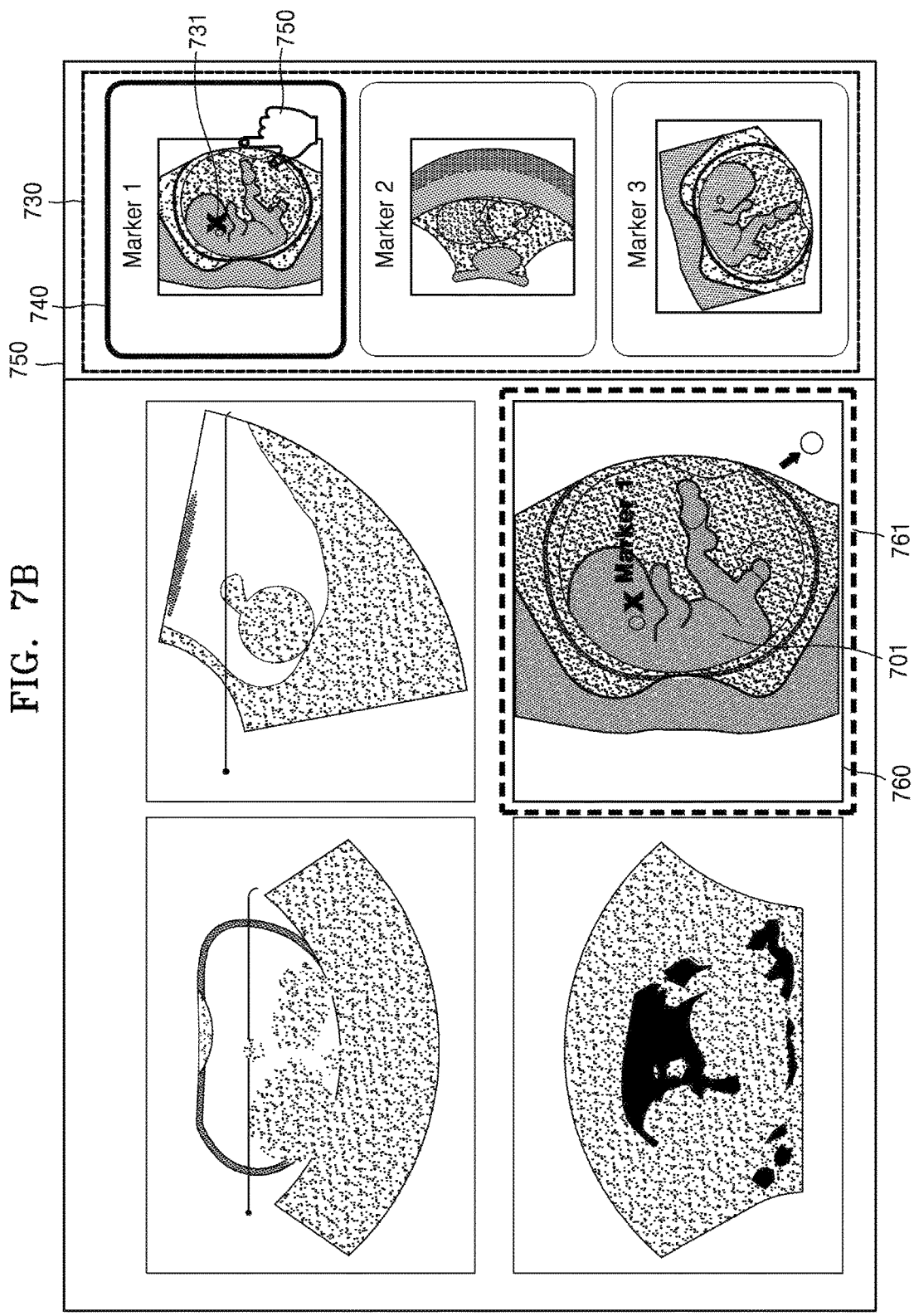
FIG. 7B is a diagram for explaining an operation of an ultrasound diagnosis apparatus according to another exemplary embodiment of the present invention.

FIGS. 7A and 7B are other diagrams for explaining an operation of the ultrasound diagnosis apparatus 200 of FIG. 2 according to an exemplary embodiment of the present invention.

FIG. 7A illustrates a first screen 710 including a first ultrasound image 720 and a marker list 730 according to an exemplary embodiment of the present invention. FIG. 7B illustrates an example of a second screen 750 including a second ultrasound image 760 and a marker list 730 according to an exemplary embodiment of the present invention.

Referring to FIG. 7A, if an object is a fetus 701, the marker list 730 may include items for at least one of first through third markers Marker 1 731, Marker 2 732, and Marker 3 733 for diagnosing abnormality in development of the fetus 701. For example, the first marker Marker 1 731 and the second marker Marker 2 732 may be set on the right side and front of the fetus 701, respectively. The third marker Marker 3 733 may be set on a side of the abdomen of the fetus 701 as shown in FIG. 7 in order to observe a part of the rear of the fetus 701 including an umbilical cord.

As shown in FIG. 7, the first ultrasound image 720 is a 3D ultrasound image representing a side of the fetus 701 and corresponding to the third marker Marker 3 733.

Referring to FIG. 7B, when a user selects an item 740 corresponding to a first marker Marker 1 731 from the marker list 730 by using a cursor 750 via the user interface unit 220, the controller 210 controls the display unit 230 to display a second ultrasound image 760 having a view corresponding to the first marker Marker 1 731. Thus, the second ultrasound image 760 having a view representing the right side of a fetus 701 is displayed on a second screen 750.

In other words, the second ultrasound image 760 representing the fetus 701, of which a view is changed to correspond to the first marker 731, may be displayed according to the user's selection of the first marker 731.

Furthermore, the item 740 corresponding to the selected first marker Marker 1 731 may be highlighted for display. As shown in FIG. 7B, the item 740 corresponding to the first marker Marker 1 731 may be displayed such that edges thereof are thicker than those of the remaining items of second and third markers Marker 2 and Marker 3. Alternatively, the item 740 of the selected first marker 731 may be displayed using a different color or shape than the remaining items. Furthermore, when the second ultrasound image 760 is output, an indicator 761 which indicates a change in an ultrasound image may be additionally displayed. This configuration may allow a user to easily interpret a selected marker and an image having a view changed according to the selected marker.

Figure 8:
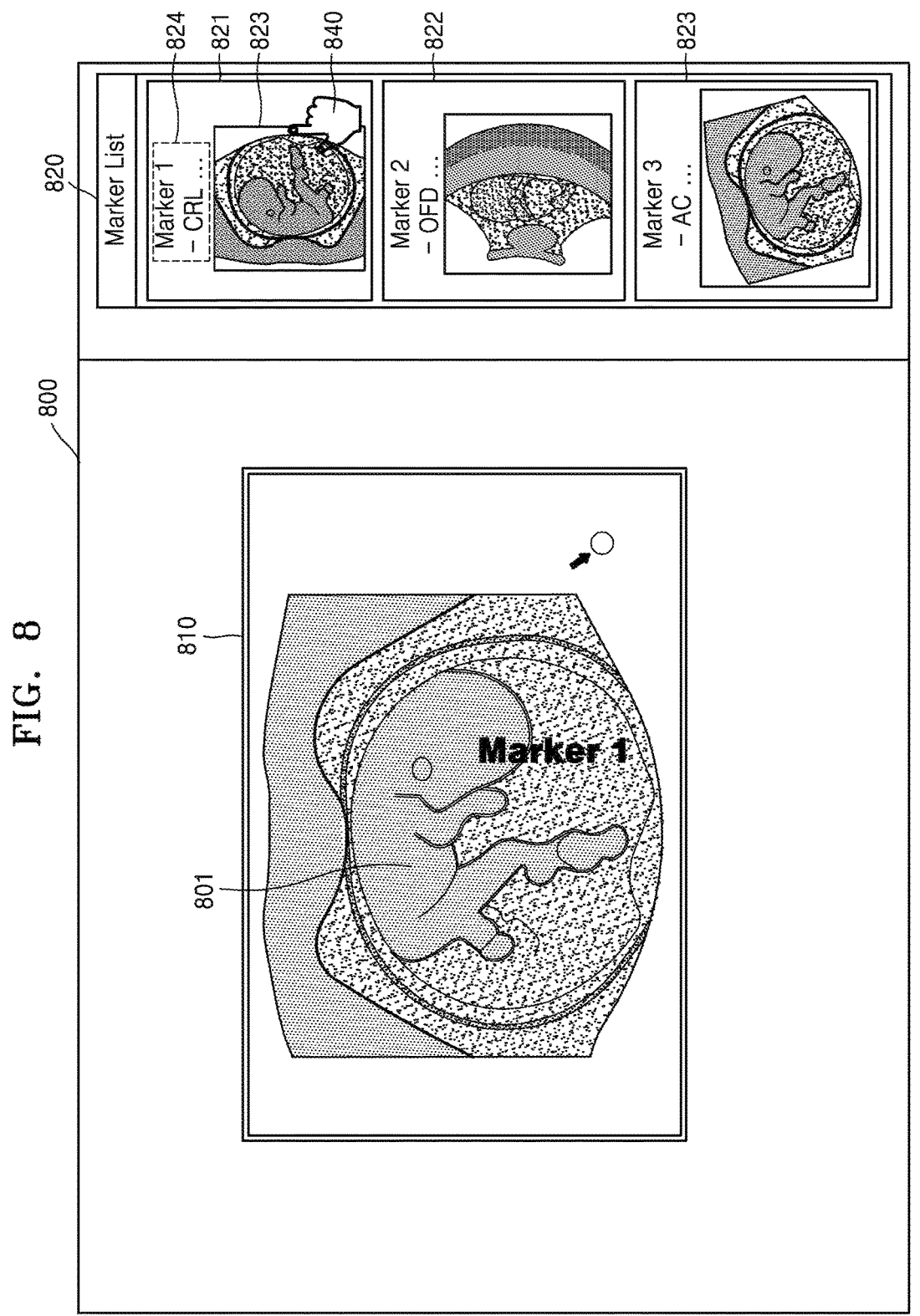
FIG. 8 illustrates a screen generated in an ultrasound diagnosis apparatus according to another exemplary embodiment of the present invention.

FIG. 8 illustrates a screen generated in the ultrasound diagnosis apparatus 200 according to another exemplary embodiment of the present invention. In detail, FIG. 8 illustrates a first screen 800 that is displayed by the display unit 230 according to a control of the controller 210, according to another exemplary embodiment of the present invention. The first screen 800 includes a first ultrasound image 810 and a marker list 820. The first screen 800 is an ultrasound image acquired by performing an ultrasound scan on a fetus 801. In FIG. 8, an object is a fetus 801, and the first ultrasound image 810 is a 3D ultrasound image.

Referring to FIG. 8, if an object is a fetus 801, the marker list 820 may include at least one marker representing a display view of the fetus 801 for measuring biometrics. Each marker item 821, 822, or 823 in the marker list 820 may include ID information (e.g., 'Marker1') of a corresponding marker displayed on the first screen 800. Furthermore, unlike in the first screen 300 shown in FIG. 3 where the first marker 321 corresponding to the first marker item 331 in the marker list 330 is displayed on the first ultrasound image 310, a marker is not displayed on the first ultrasound image 810 in the first screen 800. However, according to the present embodiment, the marker is not displayed in the first ultrasound image 800.

Referring to FIG. 8, each of the marker items 821, 822, and 823 of the marker list 820 may include at least one of ID information of a corresponding marker & information about a biometric parameter to be measured 824 (hereinafter, collectively referred to as 'information' and an image 823 having a display view needed for measurement of biometrics).

In detail, the information 824 may include biometric values that can be used to determine health conditions and normal development of the fetus 801. For example, the information about biometric parameters to be measured may include GS, CRL, BPD, HC, AC, FL, APTD, TTD, OFD, OOD, HUM, NT, and nasal bone. Such information may include information about a view for biometric measurement. For example, the information about a view for biometric measurement may include information about views for measuring fetal GS, CRL, BPD, HC, AC, FL, APTD, TTD, OFD, OOD, HUM, NT, and nasal bone. In another example, when CRL is measured on a mid-sagittal plane, the information about biometric parameters to be measured may include information regarding, for example, a 'CRL-mid-sagittal plane'.

Referring to FIG. 8, a first marker item 821 is an item corresponding to Marker 1 and may include a CRL as a biometric parameter to be measured and an ultrasound image 823 having a mid-sagittal plane as a display view for measuring the CRL.

In detail, when a user selects the first marker item 821 with a cursor 840, an ultrasound image 823 in a mid-sagittal plane for measuring a CRL may be displayed on a region where the first ultrasound image 810 has been displayed.

Figure 9A:
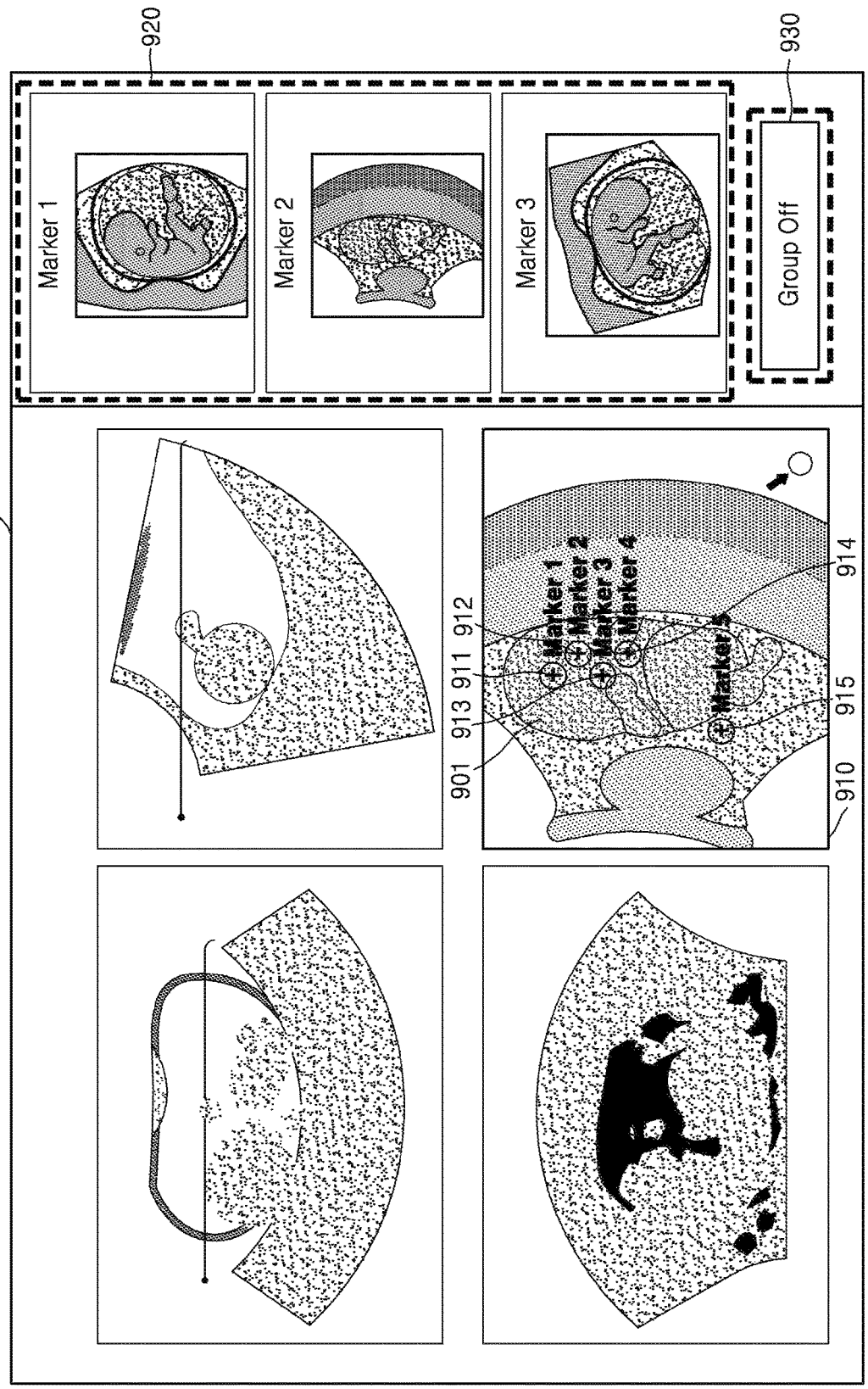
FIG. 9A illustrates a screen generated in an ultrasound diagnosis apparatus according to another exemplary embodiment of the present invention.
Figure 9B:
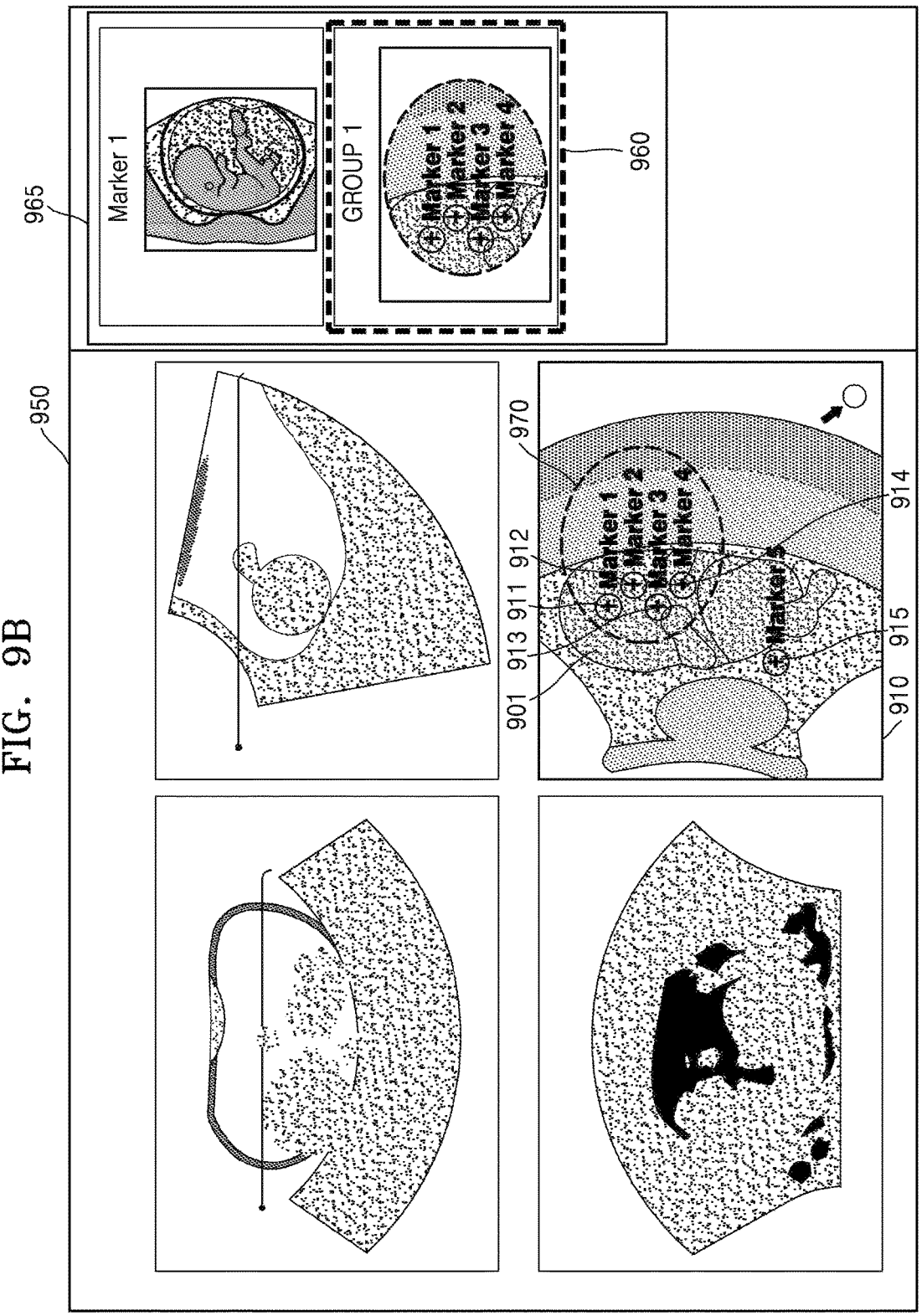
FIG. 9B illustrates a screen generated in an ultrasound diagnosis apparatus according to another exemplary embodiment of the present invention.

FIGS. 9A and 9B illustrate screens generated in the ultrasound diagnosis apparatus 200, according to another exemplary embodiment of the present invention;

The controller 210 may assigns the at least one marker to a group based on a distance between markers and generate a marker list including a sub-marker list containing the at least one marker assigned to the group.

FIG. 9A illustrates a first screen 900 displayed by the display unit 230 according to a control of the controller 210, according to another exemplary embodiment of the present invention. The first screen 900 includes a first ultrasound image 910 and a marker list 950.

Referring to FIG. 9A, the controller 210 measures distances between markers 911 through 915 and groups markers that are within a predetermined distance from one another. In detail, the controller 210 may calculate Euclidean distances between each of the markers 911 through 915 and group markers for which the Euclidean distance falls within a predetermined range.

Furthermore, the controller 210 may group markers according to each body part of an object. In detail, for each body part such as the head, face, lips, spine, GI tract, adrenal gland, kidney, bladder, external genitalia, anus, arms, hands, legs, diaphragm, or lungs, markers located at the body part may be grouped together. For example, markers located within the face of the object 901 may be clustered into a single marker group.

The first screen 900 may further include a group setting menu 930. When a user selects the group setting menu 930 via the user interface unit 220, grouping may be performed automatically. Furthermore, when markers within a predetermined distance from one another are grouped, the user may set the predetermined distance through the user interface unit 220. In addition, when markers are grouped according to each body part, the user may set a body part for which the markers are to be grouped through the user interface unit 220.

FIG. 9B illustrates a screen 950 that is output when the grouping described with reference to FIG. 9A is completed, according to an exemplary embodiment of the present invention.

For example, if the controller 210 measures distances between each of the markers 911 through 914 and groups the markers located within a predetermined distance from one another, the markers 911 through 914 located within a predetermined region 970 corresponding to the predetermined distance may be grouped together, while a marker 915 that is not within the predetermined region 970 is not grouped with markers 911 through 914.

When the grouping is completed, a marker list 965 may include a sub-marker list 960 of grouped markers. For example, if the user clicks on the sub-marker list 960, a list (not shown) of the markers 911 through 914 that belong to a predetermined group and lie within the predetermined region 970 may be subsequently displayed.

Figure 10:
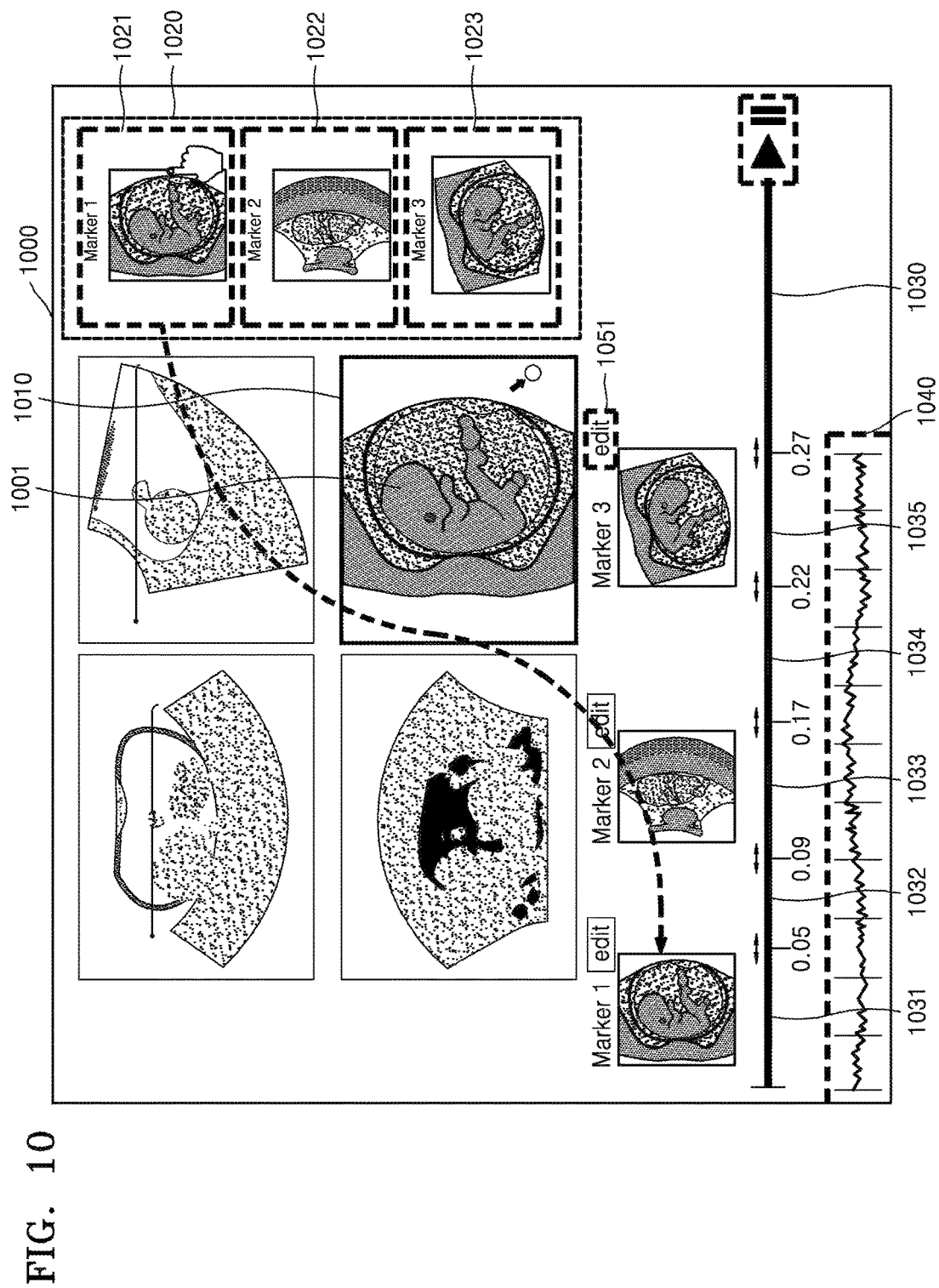
FIG. 10 is a diagram for explaining an operation of an ultrasound diagnosis apparatus according to another exemplary embodiment of the present invention.

FIG. 10 is a diagram for explaining an operation of the ultrasound diagnosis apparatus 200 according to another exemplary embodiment of the present invention. In detail, FIG. 10 illustrates a first screen 1000 displayed by the display unit 230 according to a control of the controller 210, according to another exemplary embodiment of the present invention. The first screen 1000 includes a first ultrasound image 1010 and a marker list 1020.

The user interface unit 220 may output an edit menu 1030 for generating an ultrasound moving image by using ultrasound images corresponding to a plurality of markers in the marker list 1020. Thus, the first screen 1000 may include the edit menu 1030.

In detail, the first screen 1000 may include the edit menu 1030 for generating and/or editing an ultrasound moving image by using ultrasound images corresponding to the plurality of markers. As shown in FIG. 10, the edit menu 1030 may be a cine bar for generating a moving image. The cine bar is used as a moving image editing tool. Thus, if an ultrasound moving image is located above the cine bar and a playback interval thereof is set on the cine bar, the ultrasound moving image may be reproduced during the playback interval.

Referring to FIG. 10, a user selects a first marker item 1021 and a second marker item 1022 and places them at a first time interval 1031 and a third time interval 1033, respectively. Furthermore, a second time interval 1032 is interposed between the first and third time intervals 1031 and 1033 so that there is a time gap for transition from an ultrasound image corresponding to the first marker item 1021 to an ultrasound image corresponding to the second marker item 1022. The user may also select a predetermined marker item (e.g., first marker item 1021) and place it at a predetermined time interval (e.g., first time interval 1031) by using a click and drag method.

The controller 210 may then control playback of an ultrasound moving image produced based on a plurality of second ultrasound images corresponding to a plurality of selected markers, through the edit menu. In the embodiment described above, an ultrasound image corresponding to the first marker item 1021 may be played back during the first time interval 1031, and after a lapse of the second time interval 1032, an ultrasound image corresponding to the second marker item 1022 may be played back.

Furthermore, in order to play back an ultrasound moving image, the user interface unit 220 may generate a menu 1051 for inputting at least one of playback duration of an ultrasound image corresponding to a selected marker item, information about image effects be applied to the ultrasound image, and audio information related to the ultrasound image. In addition, through the menu 1051, the user interface unit 220 may receive information about at least one of a playback duration of an ultrasound image corresponding to a selected marker item, information about image effects provided to the ultrasound image, and audio information related to the ultrasound image.

The controller 210 may then control the ultrasound diagnosis apparatus 200 so that an ultrasound moving image consisting of a plurality of ultrasound images corresponding to a plurality of selected markers is played back based on at least one of the playback duration, the information about image effects, and the audio information that are input via the menu 1051. In detail, the menu 1051 may include at least one menu item for setting or controlling at least one of control of a playback duration, editing of a playback order, editing of text added during playback of a moving image, image brightness, image contrast, transparency, rotation flip, and fade effects including fade-in and fade-out. Thus, the menu 1051 may allow a user to freely edit an ultrasound moving image.

In another example, if a user requests insertion of a fetal heartbeat sound 1040 into an ultrasound moving image via the user interface unit 220, the controller 210 may control the ultrasound diagnosis apparatus 200 so that the fetal heartbeat sound 1040 is played back together with the ultrasound moving image during time intervals set for reproducing the ultrasound moving image. For example, if the user requests playback of the fetal heartbeat sound 1040 together with the ultrasound moving image during first through fifth time intervals 1031 through 1035, the fetal heartbeat sound 1040 may be reproduced during the first through fifth time intervals 1031 through 1035. When the fetal heartbeat sound 1040 is added to the ultrasound moving image, the resulting ultrasound moving image is more vivid when reproduced.

As described above, by generating or playing back an ultrasound moving image by using ultrasound images corresponding to markers, it is possible to sequentially reproduce clinically important ultrasound images that are suited to user's intentions. Thus, according to embodiments of the present invention, a user may easily diagnose disease by using an ultrasound moving image, and a patient may conveniently listen to the user's explanation about the patient's health conditions while viewing the ultrasound image.

FIG. 11 is a flowchart of a method 1100 of displaying an ultrasound image according to an exemplary embodiment of the present invention. The method 1100 of displaying an ultrasound image according to the present embodiment includes the same operations as those performed by the ultrasound diagnosis apparatus 200 described with reference to FIGS. 1 through 10. Thus, the same descriptions as already presented with respect to FIGS. 1 through 10 are omitted.

Referring to FIG. 11, according to the method 1100, a first screen including at least one marker is displayed (operation 1110). Operation 1110 may be performed by the display unit 230 in the ultrasound diagnosis apparatus 200 of FIG. 2. In detail, a first screen that includes a marker list containing the at least one marker may be displayed. Herein, the marker list may include the at least one marker indicating a predetermined point of the object or at least one marker representing a display view of the object. Furthermore, the first screen may further include a first ultrasound image representing an object.

Selection of a predetermined marker among the displayed at least one marker list is received (operation 1120). Operation 1120 may be performed by the user interface unit 220. In detail, the user interface unit 220 may receive selection of a predetermined marker in a marker list included in the screen displayed on the display unit 230.

Following operation 1120, a view of the object may be changed according to the predetermined marker selected in operation 1120, based on position information of the predetermined marker and information about a viewpoint corresponding to the predetermined marker. Accordingly, a second ultrasound image representing an object of which a view is changed may be generated.

A second screen including the second ultrasound image that represents the object having the changed view is displayed (operation 1130). Operation 1130 may be performed by the display unit 230 according to a control of the controller 210.

As described above, an ultrasound diagnosis apparatus and a method of displaying an ultrasound image according to embodiments of the present invention are adapted to change a view of an ultrasound image corresponding to an object by selecting a marker in a marker list, thereby allowing a user to more conveniently and easily diagnose a portion of the object to be examined.

While one or more embodiments of the present invention have been described with reference to the figures, it will be understood by those of ordinary skill in the art that various changes in form and details may be made therein without departing from the spirit and essential characteristics of the present invention as defined by the following claims. Thus, it should be understood that the exemplary embodiments described therein should be considered in a descriptive sense only and not for purposes of limitation. The scope of the invention is defined not by the embodiments but by the appended claims, and all modifications or substitutions within the scope of the appended claims and their equivalents will be construed as being included in the present invention.

What is claimed is:

1. An ultrasound diagnosis apparatus comprising:
a display configured to display a first screen including a first ultrasound image, that represents an object, with at least one marker having been set within the first ultrasound image and a marker list including at least one marker item corresponding to the at least one marker;
a user interface for receiving a selection of a predetermined marker among the at least one marker; and
a controller that controls the display to display a second screen including a second ultrasound image that represents the object having a view changed from the first ultrasound image according to the predetermined marker,
wherein the controller assigns at least two markers to a group according to at least one of parts of the object and generates the marker list including a sub-marker list containing at least two marker items corresponding to the at least two markers assigned to the group,
wherein the at least one marker having been set at a predetermined point of the object or in a predetermined portion or region of the object.

2. The apparatus of claim 1, further comprising a memory for storing position information of the predetermined marker and information about a viewpoint corresponding to the predetermined marker.

3. The apparatus of claim 1, wherein the marker list comprises the at least one marker item corresponding to the at least one marker, indicating the predetermined point of the object or at least one marker representing the view of the object.

4. The apparatus of claim 1, wherein the object is a fetus, and the marker list comprises the at least one marker item corresponding to the at least one marker representing the view of the object.

5. The apparatus of claim 1, wherein the user interface unit is configured to receive from a user an input of setting a marker for adding a marker item corresponding to the marker to the marker list.

6. The apparatus of claim 1, wherein the controller assigns the at least two markers to the group based on a distance between the at least two markers and generates the marker list.

7. The apparatus of claim 1, wherein the user interface outputs an edit menu for generating an ultrasound moving image based on at least one ultrasound image corresponding to the at least one marker item included in the marker list.

8. The apparatus of claim 7, wherein the controller controls the apparatus so that the ultrasound moving image generated based on the at least one ultrasound image corresponding to the at least one marker item selected through the edit menu is played back.

9. The apparatus of claim 7, wherein in order to play back the ultrasound moving image, the user interface unit receives at least one of a playback duration of an ultrasound image corresponding to a selected marker and information about image effects applied to the ultrasound image corresponding to the selected marker via the edit menu.

10. The apparatus of claim 9, wherein the controller controls playback of the ultrasound moving image based on the playback duration, the information about image effects.

11. The apparatus of claim 1, wherein each item of the marker list comprises at least one of information about a part of the object corresponding to a marker, information about the view of the object corresponding to the marker, information about measurable biometrics corresponding to the marker, and the second ultrasound image.

12. A method of displaying an ultrasound image, the method comprising:
  displaying a first screen including a first ultrasound image, that represents an object, with at least one marker having been set within the first ultrasound image;
  assigning at least two markers to a group according to at least one of parts of the object;
  generating a marker list including at least one marker item corresponding to the at least one marker and including a sub-marker list containing at least two marker items corresponding to the at least two markers assigned to the group;
  displaying the marker list on the first screen;
  receiving a selection of a predetermined marker among the at least one marker; and
  displaying a second screen including a second ultrasound image that represents the object having a view changed from the first ultrasound image according to the predetermined marker,
  wherein the at least one marker having been set at a predetermined point of the object or in a predetermined portion or region of the object.

* * * * *